(12) United States Patent
Ledermann et al.

(10) Patent No.: US 9,500,152 B2
(45) Date of Patent: Nov. 22, 2016

(54) METHOD FOR MONITORING A BROADBAND LAMBDA PROBE

(71) Applicants: Bernhard Ledermann, Weil der Stadt (DE); Claudius Bevot, Stuttgart (DE); Rolf Reischl, Stuttgart (DE)

(72) Inventors: Bernhard Ledermann, Weil der Stadt (DE); Claudius Bevot, Stuttgart (DE); Rolf Reischl, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 276 days.

(21) Appl. No.: 14/366,948

(22) PCT Filed: Nov. 15, 2012

(86) PCT No.: PCT/EP2012/072671
§ 371 (c)(1),
(2) Date: Jun. 19, 2014

(87) PCT Pub. No.: WO2013/092018
PCT Pub. Date: Jun. 27, 2013

(65) Prior Publication Data
US 2015/0047411 A1    Feb. 19, 2015

(30) Foreign Application Priority Data
Dec. 21, 2011 (DE) .......................... 10 2011 089 383

(51) Int. Cl.
*F02D 41/14* (2006.01)
*G01N 27/419* (2006.01)
(Continued)

(52) U.S. Cl.
CPC ....... *F02D 41/1495* (2013.01); *F02D 41/1456* (2013.01); *F02D 41/222* (2013.01);
(Continued)

(58) Field of Classification Search
CPC .......... G01N 33/006; G01N 33/0036; G01N 27/4065; G01N 27/4163; G01N 27/407; F02D 41/1455; F02D 41/1456; F02D 41/1494; F02D 41/1495; F02D 41/222; G01R 31/025; F02B 39/16

USPC .................. 73/1.06; 324/543; 340/438, 635; 123/679

See application file for complete search history.

(56) References Cited

U.S. PATENT DOCUMENTS 6,200,458 B1 * 3/2001 Brida ................... G01N 27/417
                                                                  204/406
8,773,143 B2 * 7/2014 Ledermann ............. F02B 39/16
                                                                  123/679

(Continued)

FOREIGN PATENT DOCUMENTS

DE         198 00 027      7/1999
DE      10 2008 001697    11/2009

(Continued)

OTHER PUBLICATIONS

Machine translation of DE 102010028301 A1.*

*Primary Examiner* — Lisa Caputo
*Assistant Examiner* — Nathaniel Kolb
(74) *Attorney, Agent, or Firm* — Norton Rose Fulbright US LLP

(57) ABSTRACT

A method for determining a polarization of a pump cell and/or a Nernst cell of a lambda probe for the diagnosis of the broadband lambda probe. A voltage or current pulse is applied to the pump/Nernst cell in a first method task, and, in a second method task, a voltage at the pump cell and/or the Nernst cell, or a variable that is related to the polarization or its time characteristic is determined and used as a measure of the polarization, and the function of the broadband lambda probe is monitored via the ascertained polarization. The determination of the polarization may be performed as a voltage measurement performed once or multiple times, or by determining the effect of the polarization in an associated controller, such as a pump current controller of an engine control unit. The variable associated with the polarization may be the reaction of the pump current control.

8 Claims, 1 Drawing Sheet

(51) Int. Cl.
  *G01N 33/00*   (2006.01)
  *F02D 41/22*   (2006.01)
(52) U.S. Cl.
  CPC ........ *G01N27/419* (2013.01); *G01N 33/0006* (2013.01); *G01N 33/007* (2013.01); *G01N 33/0036* (2013.01); *Y02T 10/40* (2013.01)

(56) References Cited

U.S. PATENT DOCUMENTS

2005/0284772 A1* 12/2005 Farber ................ G01N 27/4065
  205/775
2010/0073017 A1* 3/2010 Bevot ................ G01N 27/4067
  324/703
2012/0293183 A1* 11/2012 Ledermann ............. F02B 39/16
  324/543

FOREIGN PATENT DOCUMENTS

| | | | |
|---|---|---|---|
| DE | 10 2010 000663 | 7/2011 | |
| DE | 10 2010 028301 | 11/2011 | |
| DE | 102010028301 A1 * | 11/2011 | ............. F01N 11/00 |
| JP | 10206371 A | 8/1998 | |
| JP | 2004526966 A | 9/2004 | |
| JP | 2004279293 A | 10/2004 | |
| WO | WO 2009135862 A1 * | 11/2009 | ......... G01N 27/4065 |

* cited by examiner

METHOD FOR MONITORING A BROADBAND LAMBDA PROBE

FIELD OF THE INVENTION

The present invention relates to a method for determining a polarization of a pump cell and/or a Nernst cell of a lambda probe for the purpose of diagnosing the broadband lambda probe.

BACKGROUND INFORMATION

The output signals of broadband lambda probes are analyzed by external circuit elements, which additionally serve the purpose of adjusting and monitoring the operating parameters of the broadband lambda probe and of monitoring the cable connections. In the process, polarization voltages that must be taken into account when adjusting the pump voltage and when analyzing the output signals occur both at the Nernst cell and the pump cell of the broadband lambda probe. Although it is possible to specify theoretical values for the polarization voltages for the various types of broadband lambda probes, the actual values deviate from these values, sometimes considerably, because of manufacturing variances and aging effects at the probe.

An improved electrical circuitry is discussed in the applicant's patent document DE 10 2008 001697 A1; in addition to operating the exhaust-gas sensor, this circuitry makes it possible to record information about the operating state of the broadband lambda probe which is used there as exhaust gas sensor, to store such information and to forward it to a superposed engine control via a digital interface. This system allows a diagnosis of the cable connections between the electrical circuit elements and the broadband lambda probe with regard to short circuits and interruptions and the maintaining of the voltages allowable at the terminals. The operational readiness of the exhaust-gas probe is detectable and its electrode polarization and aging can be monitored on a continuous basis. To carry out these measurements and to adjust the various operating states, the electrical interconnections of the broadband lambda probe differ in successive switching states of the control electronics, and the broadband lambda probe is therefore switched in different manners electrically. In the process, previous switching stays may have an effect on the measurements. For example, a switching state may lead to an undesired polarization of a Nernst cell of the broadband lambda probe, which results in a falsification of the measured value of the Nernst voltage at the Nernst cell in a subsequent switching state.

The document DE102010000663 A1 of the applicant describes a device for operating a broadband lambda probe in the exhaust tract of an internal combustion engine and for acquiring information about the operating state of the broadband lambda probe. The device makes it possible to diagnose cable connections between the electronics in order to control and analyze the signals of the broadband lambda probe with regard to interruptions and short circuits. In addition, the device makes it possible to adapt a charge exchange correction, as it may be required due of capacitances between supply lines and due to measures aimed at suppressing interference.

In the related art, the polarization of a broadband lambda probe during an active operation is able to be determined only to a highly restricted degree. However, because of aging effects at the exhaust-gas sensors, such a determination would be advantageous for improving the measuring precision at different operating points of the internal combustion engine.

SUMMARY OF THE INVENTION

It is an object of the present invention to provide a method that allows a diagnosis and consideration of a polarization voltage of a sensor element, especially a pump cell and a Nernst cell in a broadband lambda probe, during an active operation.

The object of the invention may be achieved in that a voltage or current pulse is applied to the pump cell and/or the Nernst cell in a first method step, and a voltage at the pump cell and/or the Nernst cell, or a variable that is related to the polarization or its time characteristic, is determined in a second method step and used as a measure of the polarization, and in that the function of the broadband lambda probe is monitored via the ascertained polarization. The determination of the polarization may be carried out as a voltage measurement performed once or multiple times, or by ascertaining the effect of the polarization in an associated controller, such as a pump current controller of an engine control unit. The variable associated with the polarization may be the reaction of the pump current control. The voltage measurement may take place during a phase featuring a simultaneous application of the current pulse, or in a pulse pause. For the Nernst and pump cell, the polarization may be used for diagnostic purposes. The determination of the polarization of the pump cell is able to be used to improve the precision of the lambda signal by supplementing the arithmetic rules in the associated control unit.

In one further development of the method, a voltage or current pulse is applied to the pump cell and/or the Nernst cell in a first method step, during a regular operation of the broadband lambda probe, or the regular operation of the broadband lambda probe is interrupted in the first method step and an adjusted voltage or current pulse is applied at the pump cell and/or the Nernst cell in a diagnostic cycle. The diagnosis of the broadband lambda probe is thereby able to take place during an active operation as well, so that aging is detectable and an effect of the polarization can be taken into account when determining the lambda value of the exhaust gas. The application of the current pulse may also be carried out by specifying a defined, adjusted pulse, such as it is suitable for determining a voltage jump response, for example.

If energy is supplied to the Nernst cell in the first method step, using a unidirectional current pulse, in order to set the reference pump current or to determine the internal resistance, and if the voltage at the Nernst cell or a variable related to the polarization is determined at specified times following the unidirectional current pulse in the second method step and used as a measure of the polarization of the Nernst cell, then the polarization of the Nernst cell is able to be determined during a standard mode of the broadband lambda probe. The measurement for characterizing the polarization is performed at predefined times relative to the current pulse, prior to and following the current pulse. The evaluation of the polarization in the second phase may also be undertaken via the pump current controller reacting to the Nernst voltage, taking its configuration and the arithmetic algorithm it uses into account.

In one specific embodiment of the method for determining the polarization of the pump cell, a pulse pair made up of a current pulse and a counter pulse is applied at the pump cell in the first method step, and the voltage at the pump cell is determined at predefined times in the second method step, prior to and/or following the current pulse and the counter pulse, and used as a measure of the polarization of the pump cell. The magnitude of the current pulses may be adjustable.

In one advantageous development of the method of the present invention, a pulse and a counter pulse energize the pump cell in the first method step; in a second method step, a first voltage across the pump cell is measured during a pulse pause in each case, at a specified instant following the pulse, and a second voltage across the pump cell is measured at a specified instant following the counter pulse, the difference between the first voltage and the second voltage being used as a measure of the polarization of the pump cell. In the practical implementation, voltage Up01 is determined at the unenergized pump cell in a first measuring cycle, in the presence of a stable lambda value and following a current pulse as it is used in the adjusted operation. In a second measuring cycle, following a predefined, and therefore known, current pulse, as it is used for rich gas, for example, voltage Up02 is determined at the unenergized pump cell. The difference of voltage values Up01-Up02 is a measure of the polarization of the broadband lambda probe. If the difference is small, the pump cell is classified as weakly polarized, and if the difference of the voltage values is high, it is classified as highly polarized.

One specific embodiment of the method provides that in the second method step, the voltage values at the pump cell are determined at multiple predefined times during and following the individual current pulse, and the characteristic of the voltage values or the characteristic of a variable associated with the polarization is used as a measure of the polarization of the pump cell while taking the operating parameters of the broadband lambda probe and/or exhaust-gas parameters into account. This allows a characterization of a jump response to the energization of the pump cell, its voltage characteristic supplying the information about the polarization capability of the pump cell. To evaluate the polarization capability, the temperature of the lambda probe and the composition of the exhaust gas are utilized in addition.

An identification of exhaust-gas probes requiring a polarization voltage that exceeds the permissible measure because of aging is realizable in that the polarization of the broadband lambda probe is ascertained and compared to a predefined limit value, and in that a broadband lambda probe is classified as faulty if the polarization lies above the limit value.

Interference suppressor capacitances are provided at the signal lines of the broadband lambda probe in order to dampen high-frequency interference and high-voltage introductions. If the pump current of a pump cell is set in a pulsed manner instead of an analogous time- and value-continuous manner, then a current that causes a charge exchange of the interference suppressor capacitances and additional mass-related capacitances is flowing through the pump cell in addition. This charge exchange current must be taken into account when the actual pump current is determined. However, the required correction is dependent upon the current lambda value of the exhaust gas, its temperature, and the polarization of the pump cell. Especially at the operating point of lambda=1, at which no pump current is flowing in the ideal case, non-operate currents have a particularly serious effect because of the charge exchange of the capacitances. It is therefore advantageous if the polarization of the pump cell of the broadband lambda probe is ascertained and a charge exchange correction is adjusted using the polarization.

In the following text the present invention will be explained in greater detail with reference to an exemplary embodiment shown in the figures.

DETAILED DESCRIPTION

Figure 1:
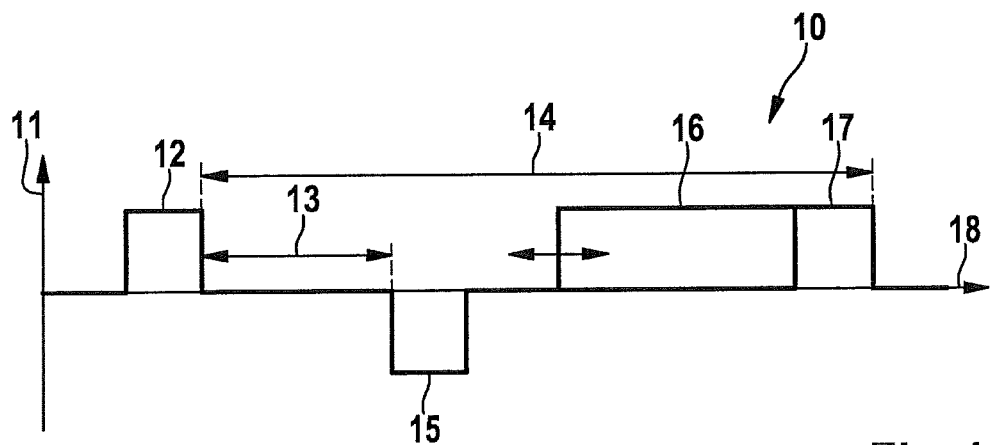
FIG. 1 shows a time-dependency diagram of a pump current of a broadband lambda probe.

Using a pump current diagram 10, FIG. 1 shows a time characteristic of a current through a pump cell of a two-cell broadband lambda probe on a current axis 11 along a first time axis 18. A period 14 of the temporal current characteristic ensues following a first current pulse 12, which comes to an end at a third current pulse 17. A first current pulse 12 is followed by a pulse pause 13, which is followed by a second current pulse 15, which has an opposite polarity to the third current pulse 17. A pulse start 16 of third current pulse 17 may be set in a time-variable manner and defines the pulse duty factor during period 14. Pulse start 16 is used to set the overall pump current through the pump cell during period 14, or to control it while taking the Nernst voltage of a Nernst cell of the broadband lambda probe into account. The aggregate pump current may additionally be adjusted by the level of current pulses 12, 15 and 17. In the present invention, current pulses 12, 15 and 17 constitute the excitation of the pump cell for the purpose of determining its polarization.

Figure 2:
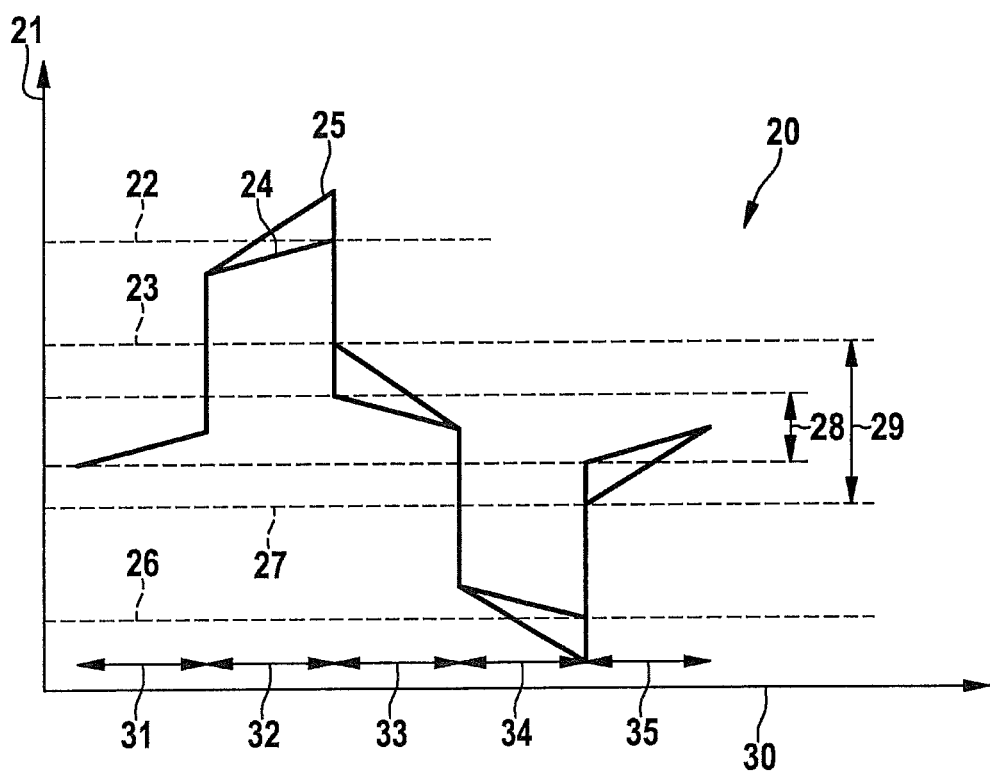
FIG. 2 shows a time-dependency diagram of the voltage at a pump cell of a broadband lambda probe.

Using a voltage diagram 20, FIG. 2 illustrates the voltage at the pump cell of the broadband lambda probe on a voltage axis 21 along a second time axis 30 during a pulse-shaped energization. In a first phase 31, a third phase 33 and a fifth phase 35, the voltage measurement is performed without an energy supply. In a second phase 32, the voltage is measured during a positive current pulse, and in a fourth phase 34, it is measured during a negative current pulse. A weakly polarized pump cell produces a first voltage characteristic 24, while a heavily polarized pump cell produces a second voltage characteristic 25. Typical of first voltage characteristic 24 is that there is a first voltage differential 28 of the voltages at the start of the non-energized third phase 33 and at the start of the likewise non-energized fifth phase 35 due to the preceding energized second phase 32 and preceding fourth phase 34, which characterizes the polarization of the pump cell. In case of a more heavily polarized pump cell featuring second voltage characteristic 25, a second voltage differential 29 comes about between the voltages at the start of non-energized third phase 33 and at the start of the likewise non-energized fifth phase 35, the second voltage differential 29 being greater than first voltage differential 28.

When compared with a predefined limit value, the evaluation of voltage differentials 28, 29 may be used to analyze the aging of broadband lambda probes and to possibly classify a probe as faulty. At the end of the energized second and fourth phases 32, 34, following first current pulse 22 and following second current pulse 26, a voltage comes about whose magnitude is a function of the polarization of the pump cell. The evaluation of entire voltage characteristic 24, 25 across energized and non-energized phases 31, 32, 33, 34 and 35 may likewise be utilized to analyze the polarization.

In case of a pulse-shaped energy supply, it will be necessary to consider mass-related capacitances at the broadband lambda probe, as they are provided as interference suppressing capacitances to dampen high-frequency interference and the introduction of high voltages at the signal lines of the broadband lambda probe, for example. The so-called charge exchange faults that occur as a result must be taken into account in a charge exchange correction for determining the correct average pump current. The charge exchange error is a function of the operating state of the internal combustion engine via the exhaust gas composition, the temperature of the exhaust gas and the broadband lambda probe, and of the polarization voltage at the pump cell. The improved determination of the polarization of the pump cell according to the present invention may therefore be used to improve the charge exchange correction as well.

What is claimed is:

1. A method for determining a polarization of at least one of a pump cell and a Nernst cell of a broadband lambda probe for diagnosing the broadband lambda probe, the method comprising:
    applying in a first task a voltage pulse or current pulse at the at least one of the pump cell and the Nernst cell;
    determining in a second task a voltage or a voltage characteristic at the at least one of the pump cell and the Nernst cell, or determining a variable that is related to the polarization or its time characteristic and used as a measure of the polarization; and
    monitoring a function of the broadband lambda probe via the polarization.

2. The method of claim 1, wherein one of the following is satisfied: (i) the current or the voltage pulse is applied at the at least one of the pump cell and the Nernst cell during a regular operation of the broadband lambda probe, or (ii) the regular operation of the broadband lambda probe is interrupted during the first task and an adjusted voltage or current pulse is applied at the at least one of the pump cell and the Nernst cell in a diagnostic cycle.

3. The method of claim 1, wherein in the first task the Nernst cell is energized by a unidirectional current pulse to set the reference pump current or to determine the internal resistance, and in the second task the voltage at the Nernst cell or a variable related to the polarization is determined at predefined times following the unidirectional current pulse and used as a measure of the polarization of the Nernst cell.

4. The method of claim 1, wherein a pulse pair made up of a current pulse and a counter pulse is applied at the pump cell in the first task, and the voltage at the pump cell is determined at predefined times prior to and/or following the current pulse and the counter pulse in the second method step and used as a measure of the polarization of the pump cell.

5. The method of claim 1, wherein the pump cell is energized by a pulse and a counter pulse in the first task, and in the second task, a first voltage across the pump cell is measured during a pulse pause at a predefined instant following the pulse, and a second voltage across the pump cell is measured at a predefined instant following the counter pulse, and the difference between the first voltage and the second voltage is used as a measure of the polarization of the pump cell.

6. The method of claim 1, wherein, in the second task the voltage values at the pump cell are determined at multiple predefined times during and following the individual current pulse, and the characteristic of the voltage values or the characteristic of a variable related to the polarization is used as a measure of the polarization of the pump cell, taking the operating parameters of the broadband lambda probe and/or exhaust-gas parameters into account.

7. The method of claim 1, wherein the polarization of the broadband lambda probe is determined and compared to a predefined limit value, and a broadband lambda probe is classified as faulty if the polarization lies above the limit value.

8. The method of claim 1, wherein the polarization of the pump cell of the broadband lambda probe is ascertained and a charge exchange correction is corrected using the polarization.

* * * * *